United States Patent [19]
Pohl et al.

[11] Patent Number: 5,851,946
[45] Date of Patent: Dec. 22, 1998

[54] COORDINATION CATALYST SYSTEMS COMPRISING INTRAMOLECULARLY STABILIZED ORGANOMETALLIC COMPOUNDS

[75] Inventors: Ludwig Pohl, Darmstadt; Eike Poetsch, Mühltal; Hans-Ludwig Hirsch, Reinheim; Herbert Schumann, Berlin; Karin Weiss, Bayreuth, all of Germany

[73] Assignee: Merck Patent Gesellschaft mit Beschrankter Haftung, Germany

[21] Appl. No.: 525,720

[22] PCT Filed: Mar. 15, 1994

[86] PCT No.: PCT/EP94/00805

§ 371 Date: Sep. 25, 1995

§ 102(e) Date: Sep. 25, 1995

[87] PCT Pub. No.: WO94/22576

PCT Pub. Date: Oct. 13, 1994

[30] Foreign Application Priority Data

Mar. 26, 1993 [DE] Germany .......... 43 09 821.5

[51] Int. Cl.$^6$ .......... C08F 4/22
[52] U.S. Cl. .......... 502/131; 502/132; 502/133; 502/200; 502/202; 502/204; 502/206; 502/209; 502/210; 502/211; 502/213; 502/219; 502/222; 502/223; 526/117; 526/118; 526/134; 526/169; 526/169.1; 526/169.2; 526/170; 526/172; 526/351; 526/352
[58] Field of Search .......... 502/131, 132, 502/133, 200, 202, 204, 206, 209, 210, 211, 213, 219, 222, 223; 526/118, 117, 134, 169, 169.1, 169.2, 170, 172, 351, 352

[56] References Cited

U.S. PATENT DOCUMENTS 3,154,528 10/1964 Kottenhahn .......... 260/80.7

*Primary Examiner*—David W. Wu
*Attorney, Agent, or Firm*—Millen, White, Zelano & Branigan, P.C.

[57] ABSTRACT

The invention relates to the use of intramolecularly stabilized organometallic compounds as components in coordination catalyst systems, corresponding coordination catalyst systems and processes for the preparation of polymers by coordination polymerization of unsaturated hydrocarbons by catalysed metathesis of alkenes and alkynes using such coordination catalyst systems.

12 Claims, No Drawings

COORDINATION CATALYST SYSTEMS COMPRISING INTRAMOLECULARLY STABILIZED ORGANOMETALLIC COMPOUNDS

The invention relates to coordination catalyst systems which comprise intramolecularly stabilized organometallic compounds. The usual coordination catalyst systems, which are usually based on transition metal compounds of sub-group IV to VIII and organometallic compounds of main group III of the Periodic Table of the Elements, are exceptionally diverse catalysts which are employed in chemical reactions of and with olefinically unsaturated compounds. These are, in particular, processes for the preparation of olefin polymers by coordination polymerization and metathesis of alkenes or alkynes. The preparation of polyethylene of increased density (high density polyethylene, HDPE) and of polymers and copolymers of ethylene, propylene or other 1-alkenes and alkynes is of considerable industrial importance. By catalysed metathesis, higher unsaturated hydrocarbon compounds can be prepared in a controlled manner from asymmetric alkenes and alkynes, and, from unsaturated cyclic hydrocarbon compounds, long-chain unsaturated hydrocarbons are obtained. The latter are used, for example, for the preparation of elastomers. Coordination catalysts, moreover, are used in other reactions, such as, for example, in alkene hydrogenation or in organometallic syntheses.

According to the current scientific knowledge on the action mechanism of coordination catalysts, it is assumed that a transition metal compound in each case forms the catalytically active center to which the olefinically unsaturated compound bonds by coordination in a first step. Olefin polymerization takes place via coordination of the monomers and a subsequent insertion reaction into a transition metal-carbon or a transition metal-hydrogen bond. The presence of organometallic compounds in the coordination catalyst systems or during the catalysed reaction is necessary in order to activate the catalyst, or maintain its activity, by reduction and, where appropriate, alkylation or formation of a complex system. These compounds are therefore also called cocatalysts. The compound containing the catalytically active transition metal atom is called the primary catalyst or precatalyst.

The best known industrially used catalyst systems for coordination polymerization are those of the "Ziegler-Natta catalyst" type and the "Phillips catalyst" type. The former comprise the reaction product of a metal alkyl or hydride of elements of the first three main groups of the Periodic Table and a reducible compound of a transition metal element of sub-group IV to VII, the combination used most frequently comprising an aluminium alkyl, such as diethylaluminium chloride, and titanium(IV) chloride. More recent highly active Ziegler-Natta catalysts are systems in which the titanium compound is fixed chemically to the surface of magnesium compounds, such as, in particular, magnesium chloride.

Chromium compounds bonded to inorganic supports are employed as a Phillips catalyst and undergo reduction or activation chiefly by organometallic compounds. Cr(II) is regarded as the catalytically active species ("reduced Phillips catalyst"). Here too, cocatalysts which are employed are chiefly aluminium alkyl compounds and alumoxane compounds.

More recent developments to give particularly efficient polymerization catalysts are directed towards metallocene compounds. Zirconocene compounds, for example, which are cyclopentadienyl complexes of zirconium alkyls or halides and derivatives thereof which are activated with the aid of aluminium, boron or phosphorus trialkyls or alumoxane, are known by the name "Kaminsky catalysts".

Use of these catalysts and related types in practice in the wide diversity of process variants developed can give products with sometimes extremely different properties. In the case of olefin polymers, which are generally known to be important as materials, the usability and use range depend, as a result of the properties, on the one hand on the nature of the monomers on which they are based and on the choice and ratio of comonomers and the typical physical parameters which characterize the polymer, such as average molecular weight, molecular weight distribution, degree of branching, degree of crosslinking, crystallinity, density, presence of functional groups in the polymer and the like, and on the other hand on properties resulting from the process, such as content of low molecular weight impurities and presence of catalyst residues, and last but not least on costs.

In addition to realization of the desired product properties, other factors are decisive for evaluating the efficiency of a coordination catalyst system, such as the activity of the catalyst system, that is to say the amount of catalyst required for economic conversion of a given amount of olefin, the product conversion per unit time and the product yield, the loss of catalyst and the reusability of the catalyst. Catalyst systems with the highest possible productivity but also with a high specificity in favor of a low degree of branching and a high stereoregularity of the polymer are therefore sought.

However, the matter of stability and easy handling of the catalyst or its components is also essential. Practically all known coordination catalysts are extremely sensitive to air and moisture. The coordination catalysts are reduced in their activity or irreversibly destroyed by access of (atmospheric) oxygen and/or water. Reduced Phillips catalysts, for example, ignite spontaneously on access of air and are then unusable. The coordination catalysts must therefore be strictly protected from access of air and moisture during preparation, storage and use, which of course makes handling difficult and increases the expenditure required.

Customary catalyst systems are also sensitive to substances which contain electron-rich elements, such as, for example, oxygen or nitrogen. Compounds such as alcohols and amines or else polar monomers, which may be of interest as comonomers or additives for the polymer, deactivate the catalyst.

The organometallic compounds to be employed as activators or cocatalysts, such as, in particular, the aluminium alkyl compounds predominantly used for this purpose, are even more sensitive in this respect and therefore even more difficult to handle. Precisely these compounds are a serious problem in practice because of their extreme sensitivity and autoignitability.

There was therefore a particular need to discover less sensitive organometallic compounds which nevertheless are suitable as activating components in coordination catalyst systems. It should be possible to render coordination catalyst systems with at least the same use properties and if possible an even wider range of use accessible with these substitute compounds. These should themselves in turn have a lower sensitivity and therefore be able to be handled with fewer problems.

It has now been found that intramolecularly stabilized organometallic compounds of the formula I $$X_1^1\text{—}M\text{—}[Z]_m \qquad (I),$$

wherein

M is an element from the group consisting of Mg, B, Al, Ga, In, Sn, Zn, Ti, Zr and lanthanides, l is the number 0, 1, 2 or 3, m is the number 1, 2, 3 or 4, where l+m corresponds to the oxidation state of M, $X^1$ is $CR^1R^2R^3$, $NR^1R^2$ or $OR^1$, $R^1$, $R^2$ and $R^3$ are H, $C_{1\text{-}6}$-alkyl, where, in the case where l=2, two radicals $R^1$ together can also form a $C_{2\text{-}6}$-alkylene bridge,

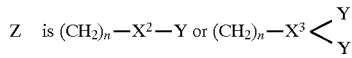

n is the number 0, 1, 2 or 3, $X^2$ is $CH_2$, NH or a 5- or 6-membered aromatic, cycloaliphatic or heteroaromatic ring, in each case substituted by Y in the o-position, $X^3$ is CH, N or a 5- or 6-membered aromatic, cycloaliphatic or heteroaromatic ring, in each case substituted with Y in the o,o'-position, Y is $(CH_2)_o$—$NR^4R^5$, $(CH_2)_o$—$PR^4R^5$, $(CH_2)_o$—$OR^4$, or $(CH_2)_o$—$SR^4$, o is the number 1, 2 or 3, and $R^4$ and $R^5$ are hydrogen or $C_{1\text{-}6}$-alkyl, with the proviso that in the case where M=B, Al, Ga or In and Z=$(CH_2)_n$—$X^2$—Y, m is not 1, are outstandingly suitable as components in coordination catalyst systems.

The invention accordingly relates to the use of intramolecularly stabilized organometallic compounds of the formula I in coordination catalyst systems.

The invention particularly relates to the use of these compounds as components in coordination catalyst systems for coordination polymerization and metathesis of alkenes and alkynes.

The invention furthermore relates to coordination catalyst systems, in particular based on transition metal compounds of sub-group IV to VIII of the Periodic Table of the Elements and organometallic compounds, these comprising at least one compound of the formula I.

The invention moreover relates to processes for the preparation of polymers by coordination polymerization and for the preparation of unsaturated hydrocarbon compounds by a catalysed metathesis reaction, in which coordination catalyst systems which comprise at least one compound of the formula I are employed.

In formula I, M is an element selected from the group consisting of magnesium (Mg), boron (B), aluminium (Al), gallium (Ga), indium (In), tin (Sn), zinc (Zn), titanium (Ti), zirconium (Zr) and the lanthanides, such as, in particular, cerium (Ce), praseodymium (Pr) and neodymium (Nd). In the compounds of the formula I, the element M is as a general rule at the particular characteristic maximum oxidation state, such as, for example, the oxidation state +II for Mg and Zn, +III for B, Al, Ga, In and the lanthanides, and +IV for Sn, Ti and Zr. These elements correspondingly carry 2 to 4 radicals $X^1$ and/or Z, at least one radical Z always being present.

$X^1$ is $CR^1R^2R^3$, $NR^1R^2$ or $OR^1$, where the radicals $R^1$, $R^2$ and $R^3$ can be hydrogen or $C_{1\text{-}6}$-alkyl. In the simplest case, $X^1$ is a hydrocarbon radical having up to 7 C atoms, which can also be branched, such as, for example, methyl, ethyl, propyl, i-propyl or t-butyl. $X^1$ can also be an amino or a hydroxyl group, which can be substituted by $C_{1\text{-}6}$-alkyl. In the case of two radicals $X^1$, these can also be bonded via an alkylene bridge having 2 to 6 C atoms.

The substituent Z carries, via a spacer grouping $(CH_2)_m$—$X^2$ or $(CH_2)_n$—$X^3$, one or two groups Y containing a heteroatom N, P, O or S in the form of an amino, phosphino, hydroxyl or thiol group, in each case optionally substituted by $C_{1\text{-}6}$-alkyl. $X^2$ and $X^3$ are bonded to the metal M directly or via an alkylene group having 1 to 3 C atoms.

$X^2$ is $CH_2$, NH or a 5- or 6-membered aromatic, cycloaliphatic or heteroaromatic ring substituted by Y in the o-position. $X^3$ is CH, N or a 5- or 6-membered aromatic, cycloaliphatic or heteroaromatic ring substituted by two radicals Y in the o,o'-position. Cyclopentyl, cyclopentenyl and cyclopentadienyl are chiefly possible as the 5-membered ring. Phenyl, 4-pyridyl, cyclohexyl, cyclohexenyl and cyclohexadienyl are chiefly possible as the 6-membered ring. $X^2$ and $X^3$ are preferably a phenyl ring.

The heteroatom of Y is bonded to $X^2$ or $X^3$ via an alkylene group having 1 to 3 C atoms.

Preferred structures of Z are

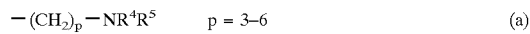

(a)

(b)

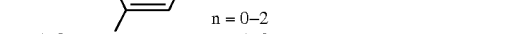

(c)

The compounds of the formula I are stabilized intramolecularly by coordinate electron transfer from the nitrogen, phosphorus, oxygen or sulphur atom of the group or groups Z to the electron-deficient metal atom M. They therefore have a high stability to (atmospheric) oxygen and moisture compared with customary metal alkyls. They are not autoigniting and are therefore easy to handle.

This stabilization is attributed to the intramolecular coordinate bond.

Typical examples of compounds of the formula I are:

Methyl-(3-dimethylaminopropyl)magnesium

Bis(3-dimethylaminopropyl)magnesium

Methyl-(3-dimethylaminopropyl)zinc

Bis(3-dimethylaminopropyl)zinc

Bis(3-diethylaminopropyl)zinc

Trimethyl(3-dimethylaminopropyl)tin

Dimethyl-bis(3-dimethylaminopropyl)tin

Dimethyl-bis(3-dimethylaminopropyl)titanium

Dimethyl-bis(3-dimethylaminopropyl)zirconium

Dimethyl(3-dimethylaminopropyl)boron

Dimethyl(3-dimethylaminopropyl)cerium

Bis-(3-dimethylaminopropyl)methylindium

Bis-(3-dimethylaminopropyl)methylaluminium

Bis-(3-dimethylaminopropyl)ethylgallium

Bis-(3-dimethylaminopropyl)ethylindium

Bis-(3-dimethylaminopropyl)ethylaluminium

Bis-(3-dimethylaminopropyl)propylgallium

Bis-(3-dimethylaminopropyl)propylindium

Bis-(3-dimethylaminopropyl)propylaluminium

Bis-(3-diethylaminopropyl)methylgallium

Bis-(3-diethylaminopropyl)methylindium
Bis-(3-diethylaminopropyl)methylaluminium
Bis-(3-dimethylaminoethyl)methylgallium
Bis-(3-dimethylaminoethyl)methylindium
Bis-(3-dimethylaminoethyl)methylaluminium
Bis-(3-diethylaminoethyl)methylgallium
Bis-(3-dimethylaminoethyl)methylindium
Bis-(3-dimethylaminoethyl)methylaluminium
Bis-(3-dimethylaminoethyl)ethylgallium
Bis-(3-dimethylaminoethyl)ethylindium
Bis-(3-dimethylaminoethyl)ethylaluminium
Bis-(3-dimethylaminobutyl)methylgallium
Bis-(3-dimethylaminobutyl)methylindium
Bis-(3-dimethylaminobutyl)methylaluminium
Bis-(3-dimethylaminobutyl)ethylgallium
Bis-(3-dimethylaminobutyl)ethylindium
Bis-(3-dimethylaminobutyl)ethylaluminium
[2,6-Bis (dimethylaminomethylene)phenyl]dimethylgallium
[2,6-Bis (dimethylaminomethylene)phenyl]dimethylaluminium
[2,6-Bis (dimethylaminomethylene)phenyl]diethylindium
[2,6-Bis (dimethylaminomethylene)phenyl]di-n-propylindium
[2,6-Bis (diethylaminomethylene)phenyl]di-n-propylindium
[2,6-Bis (diethylaminomethylene)phenyl]dimethylindium
[2,6-Bis (dimethylaminomethylene)phenyl]diethylgallium
[2,6-Bis (diethylaminomethylene)phenyl]di-n-propylgallium
[2,6-Bis (diethylaminomethylene)phenyl]dimethylgallium
[2,6-Bis (diethylaminomethylene)phenyl]diethylgallium
[2,6-Bis (diethylaminomethylene)phenyl]di-n-propylgallium
[2,6-Bis (dimethylaminomethylene)phenyl]dimethylaluminium
[2,6-Bis(dimethylaminomethylene)phenyl]diethylaluminium
[2,6-Bis (dimethylaminomethylene)phenyl]di-n-propylaluminium
[2,6-Bis(diethylaminomethylene)phenyl]dimethylaluminium
[2,6-Bis(diethylaminomethylene)phenyl]diethylaluminium
[2,6-Bis(diethylaminomethylene)phenyl]di-n-propylaluminium
[3-(1,5-Dimethylamino)pentyl]dimethylgallium
[3-(1,5-Dimethylamino)pentyl]diethylgallium
[3-(1,5-Dimethylamino)pentyl]di-n-propylgallium
[3-(1,5-Diethylamino)pentyl]dimethylgallium
[3-(1,5-Diethylamino)pentyl]diethylgallium
[3-(1,5-Diethylamino)pentyl]di-n-propylgallium
[3-(1,5-Dimethylamino)pentyl]dimethylindium
[3-(1,5-Dimethylamino)pentyl]diethylindium
[3-(1,5-Dimethylamino)pentyl]di-n-propylindium
[3-(1,5-Diethylamino)pentyl]dimethylindium
[3-(1,5-Diethylamino)pentyl]diethylindium
[3-(1,5-Diethylamino)pentyl]di-n-propylindium
[3-(1,5-Dimethylamino)pentyl]dimethylaluminium
[3-(1,5-Dimethylamino)pentyl]diethylaluminium
[3-(1,5-Dimethylamino)pentyl]di-n-propylaluminium
[3-(1,5-Diethylamino)pentyl]dimethylaluminium
[3-(1,5-Diethylamino)pentyl]diethylaluminium
[3-(1,5-Diethylamino)pentyl]di-n-propylaluminium
[4-(1,7-Dimethylamino)heptyl]dimethylgallium
[4-(1,7-Dimethylamino)heptyl]diethylgallium
[4-(1,7-Dimethylamino)heptyl]di-n-propylgallium
[4-(1,7-Diethylamino)heptyl]dimethylgallium
[4-(1,7-Diethylamino)heptyl]diethylgallium
[4-(1,7-Diethylamino)heptyl]di-n-propylgallium
[4-(1,7-Dimethylamino)heptyl]dimethylindium
[4-(1,7-Dimethylamino)heptyl]diethylindium
[4-(1,7-Dimethylamino)heptyl]di-n-propylindium
[4-(1,7-Diethylamino)heptyl]dimethylindium
[4-(1,7-Diethylamino)heptyl]diethylindium
[4-(1,7-Diethylamino)heptyl]di-n-propylindium
[4-(1,7-Dimethylamino)heptyl]dimethylaluminium
[4-(1,7-Dimethylamino)heptyl]diethylaluminium
[4-(1,7-Dimethylamino)heptyl]di-n-propylaluminium
[4-(1,7-Diethylamino)heptyl]dimethylaluminium
[4-(1,7-Diethylamino)heptyl]diethylaluminium
[4-(1,7-Diethylamino)heptyl]di-n-propylaluminium
Dimethylgallium-[bis(2-dimethylaminoethyl)]amide
Diethylgallium-[bis(2-dimethylaminoethyl)]amide
Di-n-propylgallium-[bis(2-dimethylaminoethyl)]amide
Dimethylgallium-[bis(2-diethylaminoethyl)]amide
Diethylgallium-[bis(2-diethylaminoethyl)]amide
Di-n-propylgallium-[bis(2-diethylaminoethyl)]amide
Dimethylindium-[bis(2-dimethylaminoethyl)]amide
Diethylindium-[bis(2-dimethylaminoethyl)]amide
Di-n-propylindium-[bis(2-dimethylaminoethyl)]amide
Dimethylindium-[bis(2-diethylaminoethyl)]amide
Diethylindium-[bis(2-diethylaminoethyl)]amide
Di-n-propylindium-[bis(2-diethylaminoethyl)]amide
Dimethylaluminium-[bis(2-dimethylaminoethyl)]amide
Diethylaluminium-[bis(2-dimethylaminoethyl)]amide
Di-n-propylaluminium-[bis(2-dimethylaminoethyl)]amide
Dimethylaluminium-[bis(2-diethylaminoethyl)]amide
Diethylaluminium-[bis(2-diethylaminoethyl)]amide
Di-n-propylaluminium-[bis(2-diethylaminoethyl)]amide
Dimethylgallium-[bis(2-dimethylaminopropyl)]amide
Diethylgallium-[bis(2-dimethylaminopropyl)]amide
Di-n-propylgallium-[bis(2-dimethylaminopropyl)]amide
Dimethylgallium-[bis(2-dimethylaminopropyl)]amide
Diethylgallium-[bis(2-diethylaminopropyl)]amide
Di-n-propylgallium-[bis(2-diethylaminopropyl)]amide
Dimethylindium-[bis(2-dimethylaminopropyl)]amide
Diethylindium-[bis(2-dimethylaminopropyl)]amide
Di-n-propylindium-[bis(2-dimethylaminopropyl)]amide
Dimethylindium-[bis(2-diethylaminopropyl)]amide
Diethylindium-[bis(2-diethylaminopropyl)]amide
Di-n-propylindium-[bis(2-diethylaminopropyl)]amide
Dimethylaluminium-[bis(2-dimethylaminopropyl)]amide Diethylaluminium-[bis(2-dimethylaminopropyl)]amide
Di-n-propylaluminium-[bis(2-dimethylaminopropyl)]amide
Dimethylaluminium-[bis(2-diethylaminopropyl)]amide
Diethylaluminium-[bis(2-diethylaminopropyl)]amide
Di-n-propylaluminium-[bis(2-diethylaminopropyl)]amide Most of the intramolecularly stabilized organometallic compounds of the formula I are known as such per se. Such compounds are thus described, for example, in DE 4213292, DE 4109723 and in DE 3913165. It can also be seen from the documents mentioned that the compounds are stable to air and moisture.

However, they are proposed only for use for the preparation of thin semiconductor layers of metal or compound by gas-phase deposition. No indication of the suitability of these compounds as activating components in coordination catalyst systems for olefin polymerization or metathesis is to be found in these documents.

The compounds of the formula I are prepared by methods known per se, such as are described in the literature (for example G. Bähr, P. Burba, Methoden der Organischen Chemie (Methods of Organic Chemistry), Volume XIII/4, Georg Thieme Verlag, Stuttgart (1970)), and in particular under reaction conditions which are known and suitable for the reactions mentioned. It is also possible to use variants which are known per se and are not mentioned here.

These compounds can thus be prepared, for example, by reacting metal alkyl chlorides with an alkali metal organyl of the corresponding Lewis base or a Grignard compound in an inert solvent.

Further details on the synthesis of such compounds can be found in the abovementioned patent documents or Z. anorg. allg. Chem. 462, 152 (1980) and 505, 127 (1983).

When the compounds of the formula I are employed according to the invention as activating components in coordination catalyst systems, it has been found, surprisingly, that the catalyst systems as a result react less sensitively to (atmospheric) oxygen and moisture, so that such strict safety measures such as are necessary in the case of coordination catalysts activated with-customary aluminium alkyls do not have to be taken.

This finding is particularly surprising and unforeseeable, especially since the use of structurally similar intramolecularly stabilized organoaluminium compounds, such as, for example, (3-diethylaminopropyl)-di-isobutylaluminium, in certain coordination catalyst systems is already known. U.S. Pat. No. 3,154,528 discloses coordination catalyst systems which are based on vanadium tetrachloride and are activated with such compounds, but which are described as just as sensitive to air and moisture as customary coordination catalyst systems. JP 60-240706, JP 61-007305, JP 61-252205, JP 62-100505 and JP 62-138506 disclose coordination catalyst systems based on titanium compounds which likewise comprise such organoaluminium compounds and also other compounds which function as electron donors but which are initially activated with customary aluminium alkyls. Because of the presence of the latter, these catalyst systems are likewise extremely sensitive and require the usual strict safety measures.

In the coordination catalyst systems according to the invention, moderate access of air, oxygen or moisture does not result in destruction or a drastic reduction in activity. Corresponding coordination catalyst systems based on chromium bonded to a support do not ignite in air, for example, but continue to be readily usable without change. This has the very advantageous consequence that the handling of the coordination catalyst systems according to the invention during preparation, storage and use is considerably less problematic. The expensive exclusion of even traces of air, oxygen and moisture in the solvents, monomers and inert gases employed during the polymerization can therefore be dispensed with.

The compounds of the formula I to be employed according to the invention in coordination catalyst systems, moreover, have the effect of further advantageous results when used as specified in polymerization processes and metathesis reactions. The corresponding coordination catalyst systems according to the invention thus generally show an extremely high activity and productivity. This has the result that more product is formed with the amount of catalyst employed, or the required amount of catalyst can be reduced accordingly. Advantageous consequences of this are that correspondingly less catalyst must be removed from the product, or products with a lower residual content of catalyst are obtained, and, last but not least, that the costs are also reduced because of less consumption of catalyst. Numerous other factors of course also have an influence here, such as the qualitative and quantitative composition of the catalyst system, the nature of the monomers and the composition during the copolymerization of monomer mixtures, reaction conditions and the procedure during the polymerization. However, the expert can easily determine and optimize the catalyst system which is the most suitable for his purposes with the aid of routine experiments.

Furthermore, a pronounced specificity in the direction of high molecular weights and narrower molecular weight distributions is found for the coordination catalyst systems according to the invention in the case of olefin polymerization. These findings also depend on additional factors, such as the composition of the catalyst system, the nature of the monomers and the process conditions used, but can easily be optimized for the particular application.

In alkene polymerization, the catalysts according to the invention can have a pronounced stereoselective action in the direction of isotactic polymers in a given case. Particular stereoisomers or products having a particular configuration can be formed preferentially by metathesis or ring-opening metathesis polymerization. This stereoselectivity can furthermore be influenced by controlled structuring of the compounds of the formula I. For example, in formula I, if the radicals $R^1$, $R^2$ and $R^3$ are each different from one another in the case where $X^1$ is $CR^1R^2R^3$, the radical $X^1$ has an asymmetric C atom, which can cause stereoselective induction in the polymerization or metathesis of 1-alkenes.

Coordination catalyst systems which comprise the cyclic organometallic compounds of the formula I according to the invention are preferably suitable for the polymerization of 1-alkenes and 1-alkynes, it being possible to obtain both homopolymers from uniform monomers and copolymers from monomer mixtures. They are furthermore suitable for the metathesis of 1-alkenes and 1-alkynes and for ring-opening metathesis of cyclic alkenes.

Coordination catalyst systems of the "Ziegler-Natta" and of the "Phillips" type which are activated with the compounds of the formula I according to the invention as cocatalysts furthermore show the surprising property that polar olefinically unsaturated monomers can also be polymerized with them. As is known, essentially only 1-alkenes and 1-alkynes can be polymerized with conventional catalyst systems. Styrene, for example, can scarcely be subjected to coordination polymerization, and even more polar monomers, such as vinyl compounds and acrylic acid derivatives, cannot be subjected to coordination polymerization at all. This probably lies in the fact that these polar compounds deactivate the metal atoms of the primary catalyst and/or cocatalyst by a strong coordinate bond. As a result of the intramolecular coordinate saturation in the compounds of the formula I, however, this is no longer possible, which explains the remarkable activity of the catalyst systems according to the invention with respect to polar monomers.

The compounds of the formula I are used according to the invention as activating components in coordination catalyst systems completely analogously to and as a substitute for the metal organyls customary to date and in particular the sensitive and hazardous aluminium alkyls. Because of the increased activity, the content of organometallic compound in the catalyst system and also the amount of catalyst in the reaction can be reduced. The catalysts are prepared and used in a manner known per se, such as is customary for the particular system and the particular use. As a rule, olefin polymerization and metathesis are carried out by the suspension process under heterogeneous catalysis. For this, the precatalyst bonded to a support is first prepared from the catalytically active transition metal compound and a finely divided support material, and this is activated or preactivated in the customary manner, if necessary, and then suspended in a solvent, for example in an alkane hydrocarbon, such as pentane or hexane.

The addition of the cocatalyst is carried out, as is otherwise also customary, immediately before the reaction of the monomers or "in situ" in the presence thereof. The control of the reaction and the isolation and working-up of the reaction products are likewise carried out in a completely analogous manner. As already mentioned, because of the stability of the compounds of the formula I and the lower sensitivity of the resulting catalyst systems, all these actions can be carried out with considerably fewer problems and with considerably less strict protective and safety measures.

New coordination catalyst systems with advantageous properties and a considerably wider range of use, which furthermore can be tailored to the particular requirements of the application, are thus rendered accessible by the invention.

EXAMPLE 1

A solution of 38.2 g (0.28 mol) of zinc chloride in 100 ml of tetrahydrofuran is added dropwise at room temperature to a Grignard reagent prepared from 24.3 g (1.0 mol) of magnesium and 102.1 g (0.84 mol) of 3-dimethylaminopropyl chloride in 500 ml of tetrahydrofuran, and the mixture is then heated at 70° C. for 2 hours. After cooling, insoluble material is separated off by filtration, the solvent is removed and the residue is distilled in vacuo. Bis(3-dimethylaminopropyl)zinc is obtained as a crystalline solid having a melting point of 40° C. and a boiling point of 68° C./0.1 mbar.

EXAMPLE 2

6.8 g (0.05 mol) of zinc chloride in 100 ml of tetrahydrofuran are added at room temperature to a Grignard reagent prepared from 4.9 g (0.2 mol) of Mg and 19.4 g (0.16 mol) of 3-diethylaminopropyl chloride in 100 ml of tetrahydrofuran. When the reaction has ended, the mixture is stirred at room temperature for 24 hours and filtered, the solvent is removed and the residue is distilled in vacuo. Bis(3-diethylaminopropyl)zinc is obtained as a colourless liquid having a boiling point of 103° C./0.1 mbar.

EXAMPLE 3

A Grignard reagent is prepared from 6.1 g (0.25 mmol) of Mg and 24.3 g (0.2 mol) of 3-diethylamino-propyl chloride in 100 ml of tetrahydrofuran. About 80 ml of tetrahydrofuran are then removed, and 50 ml of pentane are added to the concentrated solution. The magnesium chloride which has precipitated out is removed by filtration and the residue is distilled in vacuo. Bis(3-dimethylaminopropyl)magnesium is obtained as a white solid having a boiling point of 170°C./0.05 mbar.

EXAMPLE 4

3.0 mmol of 2,6-bis(dimethylaminomethylene)phenyllithium are obtained from 0.82 g (3.0 mmol) of 2,6-bis-(dimethylaminoethylene)phenyl bromide and 1.9 ml of n-butyllithium (3.0 mmol; 1.6 mol/l in hexane), are added to a solution of 0.4 g (3.0 mmol) of dimethylgallium chloride in 10 ml of hexane. After the mixture has been stirred at room temperature for 12 hours, it is filtered, the solvent is stripped off in vacuo and the residue is sublimed in vacuo. [2,6-Bis(dimethylaminomethylene)-phenyl] dimethylgallium is obtained as colourless crystals, melting point 34° C.

EXAMPLE 5

Analogously to Example 4, [2,6-bis(dimethylaminomethylene)phenyl]dimethylindium is obtained from 2.71 g (10.0 mmol) of 2,6-bis(dimethylaminomethylene)phenyl bromide in 40 ml of hexane, 6.3 ml of n-butyllithium (10.0 mmol; 1.6 mol/l in hexane) and 1.8 g (10.0 mmol) of dimethylindium chloride in 20 ml of hexane, and, by cooling a concentrated hexane solution to −30° C., is isolated in the form of colourless crystals, melting point 53° C.

EXAMPLE 6

Analogously to Example 4, [2,6-bis(dimethylaminomethylene)phenyl]diethylindium is obtained from 2.5 g (9.2 mmol) of 2,6-bis(dimethylaminomethylene)phenyl bromide in 40 ml of hexane, 5.8 ml of n-butyllithium (9.2 mmol; 1.6 mol/l in hexane) and 1.92 g (10.0 mmol) of diethylindium chloride in 20 ml of hexane, and is isolated in the form of colourless crystals, melting point 41° C.

EXAMPLE 7

Analogously to Example 4, [2,6-bis(dimethylaminomethylene)phenyl]di-n-propylindium is obtained from 2.2 g (8.1 mmol) of 2,6-bis(dimethylaminomethylene)phenyl bromide in 40 ml of hexane, 5.1 ml of n-butyllithium (8.1 mmol; 1.6 mol/l in hexane) and 1.90 g (8.1 mmol) of di-n-propylindium in 20 ml of hexane, and is isolated by vacuum distillation as a colourless liquid, boiling point 125° C./0.03 mbar.

EXAMPLE 8

Analogously to Example 4, [2,6-bis(diethylaminomethylene)phenyl]diethylindium is obtained from 2.4 g (7.3 mmol) of 2,6-bis(diethylaminomethylene)phenyl bromide in 40 ml of hexane, 4.6 ml of butyllithium (7.3 mmol; 1.6 mol/l in hexane) and 1.5 g (7.3 mmol) of diethylindium chloride in 20 ml of hexane, and is isolated by vacuum distillation as a colourless liquid, boiling point 115° C./0.04 mbar.

EXAMPLE 9

5 g of 3-dimethylaminopropyllithium (53.7 mmol) are suspended in 40 ml of pentane, and a solution of 4 g of methylgallium dichloride (25.7 mmol) in 20 ml of benzene is added dropwise. The mixture is first stirred at room temperature for one hour and then boiled under reflux for 6 hours. After cooling, the lithium chloride and excess lithium salt are filtered off and the solvent is stripped off in vacuo. The residue which remains is sublimed in vacuo at an oil bath temperature of 60° C. Bis-(3-dimethylaminopropyl) methylgallium is obtained as a white solid of melting point 52° C.

EXAMPLE 10

5.45 g of $ZrCl_4$ are added to a solution of 8.71 g of 3-dimethylaminopropyllithium in 150 ml of diethyl ether at a temperature of −5° C. with exclusion of light, the mixture is then stirred for one hour, and thereafter the solvent is removed in vacuo. The residue is extracted several times with n-pentane. The combined extracts are filtered and the filtrate is cooled to a temperature of −78° C., whereupon colourless needles of tetrakis(3-di-methylaminopropyl) zirconium separate out.

We claim:

1. A coordination catalyst system which comprises an intramolecularly stabilized organometallic compound of the formula I $$X^1{}_l-M-(Z)_m \qquad (I),$$

wherein

M is an element selected from the group consisting of Mg, B, Al, Ga, In, Sn, Zn, Ti, Zr and lanthanides, l is the number 0, 1, 2 or 3, m is the number 1, 2, 3 or 4, where l+m corresponds to the oxidation state of M, $X^1$ is $CR^1R^2R^3$, $NR^1R^2$ or $OR^1$, $R^1$, $R^2$ and $R^3$ are H, $C_{1-6}$-alkyl, where, in the case where l=2, two radicals $R^1$ together can also form a $C_{2-6}$-alkylene bridge, Z is $$(CH_2)_n-X^2-Y \text{ or } (CH_2)_n-X^3\diagup_Y^Y$$

n is the number 0, 1, 2 or 3, $X^2$ is $CH_2$, NH or a 5- or 6-membered aromatic, cycloaliphatic or heteroaromatic ring, in each case substituted by Y in the o-position, $X^3$ is CH, N or a 5- or 6-membered aromatic, cycloaliphatic or heteroaromatic ring, in each case di-substituted with Y in the o,o'-positions, Y is $(CH_2)_o-NR^4R^5$, $(CH_2)_o-PR^4R^5$, $(CH_2)_o-OR^4$, or $(CH_2)_o-SR^4$, o is the number 1, 2 or 3, and $R^4$ and $R^5$ are hydrogen or $C_{1-6}$-alkyl, with the proviso that in the case where M=B, Al, Ga or In and $Z=(CH_2)_n-X^2-Y$, m is not 1.

2. A coordination catalyst system of claim 1, which further comprises a transition metal compound of the subgroups IV to VIII of the Periodic Table of Elements.

3. A process for the preparation of a polymer which comprises coordination polymerizing one or more alkenes and/or alkynes in the presence of a coordination catalyst system of claim 1.

4. A process for the preparation of a polymer which comprises coordination polymerizing one or more alkenes and/or alkynes in the presence of a coordination catalyst system of claim 2.

5. A process for the preparation of an unsaturated hydrocarbon compound which comprises metathesis reacting of at least one alkene and/or alkyne in the presence of a coordination catalyst system of claim 1 as the metathesis catalyst.

6. A process for the preparation of an unsaturated hydrocarbon compound which comprises metathesis reacting of at least one alkene and/or alkyne in the presence of a coordination catalyst system of claim 2 as the metathesis catalyst.

7. The process of claim 3, wherein the polymer prepared is a polymer or copolymer of ethylene, propylene and/or other 1-alkenes.

8. The process of claim 3, wherein the one or more alkenes and/or alkynes include polar olefinically unsaturated monomers.

9. A coordination catalyst system of claim 1, wherein the element M is in the maximum oxidation state for that element.

10. A coordination catalyst system of claim 1, wherein $X^2$ and $X^3$ are selected from the group consisting of cyclopentyl, cyclopentenyl, cyclopentadienyl, phenyl, 4-pyridyl, cyclohexyl, cyclohexenyl and cyclohexadienyl.

11. A coordination catalyst system of claim 1, wherein $X^2$ and $X^3$ are phenyl.

12. A coordination catalyst system of claim 1, wherein at least one group Z is of one of the following formulae (a), (b) or (c):

$-(CH_2)_p-NR^4R^5 \qquad p = 3-6 \qquad$ (a)

(b)

$-(CH_2)_n-\phantom{x}\diagup\phantom{x}$
$R^4R^5N-(CH_2)_o \qquad n = 0-2$
$\qquad\qquad\qquad o = 1-2$ $R^4R^5N-(CH_2)_o \qquad$ (c)

$-(CH_2)_n-\phantom{x}\diagup\phantom{x}$ $R^4R^5N-(CH_2)_o \qquad n = 0-2$
$\qquad\qquad\qquad o = 1-2.$

* * * * *